US00PP11658P

United States Patent [19]

Kent

[11] Patent Number: Plant 11,658

[45] Date of Patent: Nov. 28, 2000

[54] BROMELIAD PLANT NAMED 'GUZ 217'

[75] Inventor: Jeffrey C. Kent, Vista, Calif.

[73] Assignee: Kent's Bromeliad Nursery, Inc., Vista, Calif.

[21] Appl. No.: 09/114,407

[22] Filed: Jul. 13, 1998

[51] Int. Cl.[7] ..... A01H 5/00

[52] U.S. Cl. ..... Plt./371

[58] Field of Search ..... Plt./371

[56] References Cited

U.S. PATENT DOCUMENTS

P.P. 9,476 3/1996 Kent ..... Plt./371

P.P. 10,069 10/1997 Kent ..... Plt./371

*Primary Examiner*—Bruce R. Campell
*Assistant Examiner*—Wendy A Baker
*Attorney, Agent, or Firm*—James A. Lucas; Driggs, Lucas, Brubaker & Hogg Co., L.P.A.

[57] ABSTRACT

A Guzmania hybrid having leaf variegation which is regular in placement. The variegation contributes to an appearance which is lighter and brighter than other variegated hybrids. The bract color remains for two to three months when the plant is maintained under indoor lighting conditions.

1 Drawing Sheet

BACKGROUND OF THE INVENTION

The present invention relates to a new and distinct variety of plant in the genus Guzmania within the Bromeziaceae family. This application relates to a newly developed interspecific hybrid Guzmania plant resulting from a planned breeding program which I conduct on an ongoing basis. The object of the breeding program includes the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Included objects of my program are to produce plants which will be attractive to the consumer; which will develop reasonably rapidly under controlled conditions; and, retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by division while continuing the distinctive characteristics of the plants through progressive clonal generations.

SUMMARY OF THE INVENTION

The plant of this disclosure was a variegated product of division of a sport of the parent genus Guzmania 'Grand Prix' (unpatented) which is a hybrid of the seed parent *Guzmania minor* 'Red' (unpatented) and the pollen parent *Guzmania wittmackii* 'Red/Orange Equador' (unpatented). The plant was a naturally occurring, vegetative sport discovered as a single plant growing in a cultivated planting of 'Grand Prix'. With the recognition that this sport satisfied the objects of the breeding program, it was isolated and set aside for further observation and testing. The resulting selection has been assigned the designation 'GUZ 217' for purposes of identification. This plant has been reproduced by division at Vista, Calif., and elsewhere, and the clonal specimens resulting have been determined to be identical to the original selection in all distinguishing characteristics. The superior attributes of this plant will be revealed in the botanical description to follow.

The plant 'GUZ 217' has an overall height from the soil surface of about 18" to 20" when finished to a stage of full bloom, and a spread of about 30" to 32". The leaves are light green, smooth, evenly variegated with white variegations giving the plant an overall effect of being lighter and brighter when compared to other variegated hybrids known to me such as Guzmania 214 'Amethyst'. U.S. Plant Pat. No. 9,476 which has leaves of a darker blue green with creamy white variegations. The leaves reach a length of about 18¾ inches. The width of the leaves is about 2 inches as compared to the leaves of 'Amethyst' which are about 1 inch in width.

Inflorescence is typical in character of Guzmania 'Grand Prix'; floral bracts are translucent yellow color at base and terminus. The staining is red-yellow elsewhere, as contrasted with Amethyst which is stained red purple. The scape bracts are stained at base of inflorescence, becoming solid at the terminus of scape bracts covering the variegation.

The attractive bright red bract color has a high sheen and the bract coloration is retained under subdued interior lighting conditions for more than two months.

BRIEF DESCRIPTION OF THE VIEW OF THE DRAWING

The single color photograph of the drawing depicts a mature specimen of the plant in side perspective angle in mid to late flowering stage. Illustrated are the mature leaves and the spike. The relative sizes of the lower, splayed intermediate and terminal bracts can be seen by the angle of the illustration.

The color definitions in the specification have been taken from the R.H.S. Colour Chart of The Royal Horticultural Society. While the colors depicted are believed to be of a high level of color fidelity, the coloration of this plant should be understood to be approximate, and somewhat variable as a function of cultural conditions and horticultural practices. For example, the bract color might slightly fade if the plant is cultured in bright light; the leaf color can be varied by the composition and concentration of fertilizer applied to specimens of the plant, and age of the specimens.

The time period from liner to market stage is approximately two years. The plant has a prolific propensity to develop side-shoots with the general number of leaves and bracts being about 16 when produced for optimum market stage.

BOTANICAL DESCRIPTION OF THE PLANT

Propagation:

*Method of asexual reproduction.*—Division.

*Where reproduction took place.*—Kent's Bromeliad Nursery, 1266 Ridge Road, Vista, Calif. 92083.

Plant: Monocot Perennial. Medium in size.

*Overall height from soil surface including inflorescence.*—18" to 20".

*Overall width.*—30" to 32".

Vigorous in growth to anthesis relative to other variegated Guzmania cultivars. Upright, spreading and dense. Vase formed. Tender Hardiness at temperatures below 32° F. This variety has resistance to plant diseases comparable to other variegated Guzmania cultivars.

Leaves:

*Length.*—18¾".

*Width.*—2".

Medium in size. Linear and acutely pointed.

*Coloration.*—The background is 147A on the obverse, 147B on the reverse. The leaf is variegated longitudinally. The coloration of the variegation is 157D with irregular areas that are 57C in color. This 57C coloration appears as clear lines on younger leaves and as a diffuse stain on older leaves. The irregular 57C coloration may appear at any location (i.e. from base to tip) of the leaf but is visible only in the variegated portions of the leaf.

Medium thickness. Light to medium green color. Smooth.

*Margin.*—Smooth.

*Scape bracts.*—Lanceolate in shape terminating in a narrow acuminate tip, clasping 4¾"×1½" decreasing to 3"×¾" at terminus. Tips of lower scape bracts having a broad stripe, 147-A in color, at margin; Upper scape bract solid in color with no variegation; some bracts tipped 45-A in color when further advanced in flowering process.

*Coloration.*—The bract base is 8D in color, intensifying in coloration to a darker yellow such as 8B moving towards the central portion of the bract. The central portion of the bract is a blend of 8B and 46C, both appearing in clear-cut lines. Progressing towards the tip, the bract becomes 46C in color — with any portion of the last approximately 1¼" of the tip varying in coloration from 46C to resembling any permutation of the leaf coloration as recited above.

*Floral bracts.*—2½"×⅜" at base. Translucent, colored 6-D at base 46-D throughout. Inflorescence a branched spike.

Flowers: Cylindrical corolla, 8-D at anthesis Three sepals 2"×¼" transparent at base, 39-B in mid-section and 39-D at the obtuse tip Three petals, obtuse scarely open at anthesis 2"×3/16", joined 1¾" from the base. Flower buds are 1½"×5/16" cylindrical tapering to a point (roughly lanceolate), 155D in color.

Fruit: A three celled capsule, splitting longitudinally when mature, with pappus.

What is claimed is:

1. A new and distinct variety of Guzmania plant as shown and described herein, characterized in leaves that are a medium light green with white variegation which is regular in placement, and red-orange staining which gives an overall appearance of the plant which is lighter and brighter than other variegated hybrids.

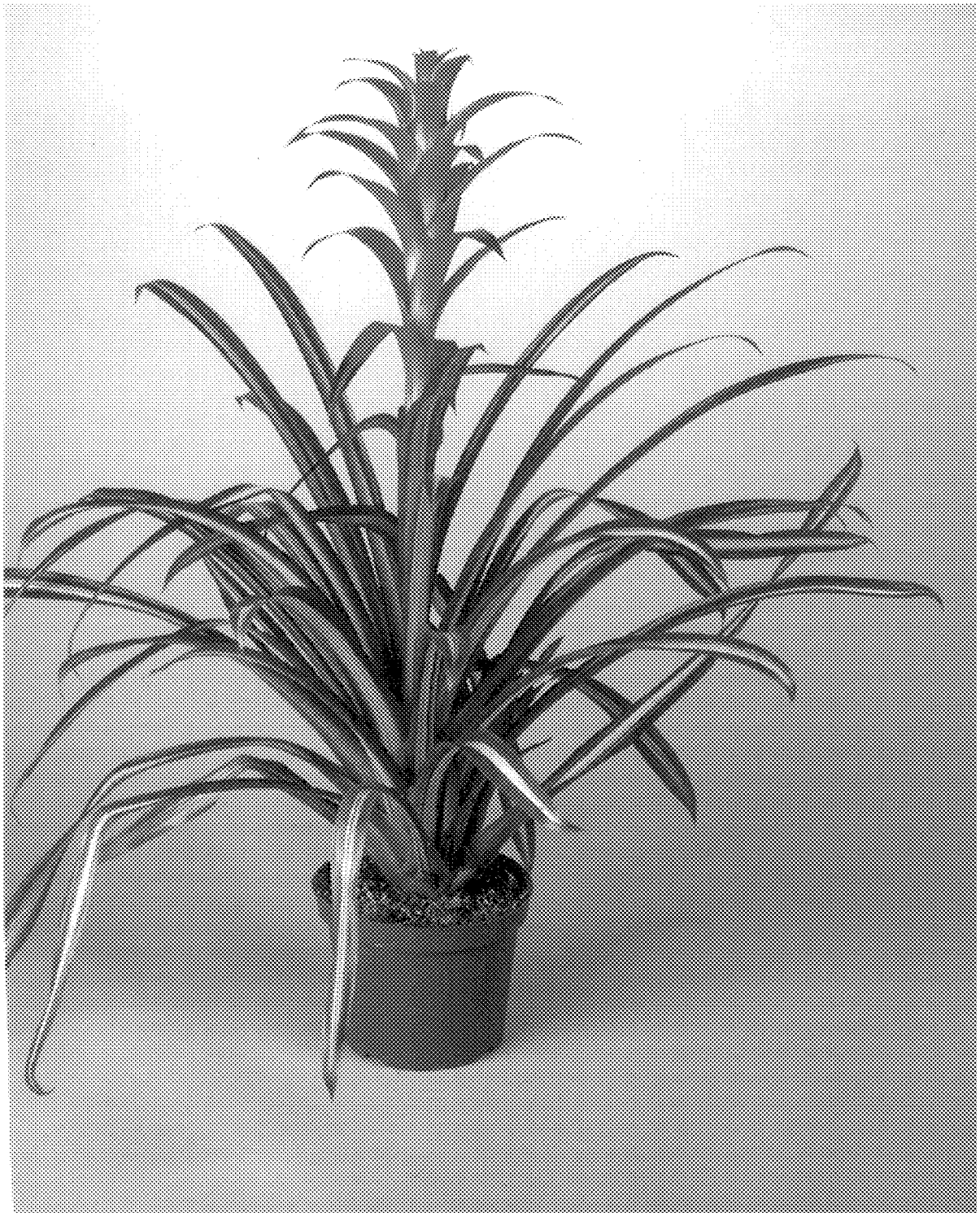

* * * * *